US008350068B2

(12) United States Patent
Rosas et al.

(10) Patent No.: US 8,350,068 B2
(45) Date of Patent: Jan. 8, 2013

(54) LIQUID-LIQUID EXTRACTION PROCESS FOR THE PURIFICATION OF ESTOLIDES FOR USE AS LUBRICANTS

(75) Inventors: Danielle de Oliveira Rosas, Rio de Janeiro (BR); Bauer Costa Ferrera, Proto Alegre (BR); Denise Diniz Leite, Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 29 days.

(21) Appl. No.: 12/667,177

(22) PCT Filed: Jun. 26, 2009

(86) PCT No.: PCT/GB2009/001607

§ 371 (c)(1), (2), (4) Date: Jun. 7, 2010

(87) PCT Pub. No.: WO2010/001098

PCT Pub. Date: Jan. 7, 2010

(65) Prior Publication Data

US 2011/0092723 A1 Apr. 21, 2011

(30) Foreign Application Priority Data

Jun. 30, 2008 (BR) ..................................... 0803361

(51) Int. Cl.
*C07C 69/74* (2006.01)

(52) U.S. Cl. ...................................................... 554/122
(58) Field of Classification Search .................. 554/122
See application file for complete search history.

(56) References Cited

U.S. PATENT DOCUMENTS 2,822,331 A * 2/1958 Dilworth et al. ............. 508/465

FOREIGN PATENT DOCUMENTS

WO WO 0153247 A1 * 7/2001

OTHER PUBLICATIONS

Cermak, S. C., and Isbell, T. A.: "Synthesis and physical properties of mono-estolides with varying chain lengths" Industrial Crops and Products., vol. 29, Jun. 20, 2008, pp. 205-213.*

Noble, W.R., Eisner, A., and Scanlan, J.T. : "Isolation of an Hydroxy Acid Concentrate from Wool Wax Acids" Journal of the American Oil Chemists' Society., vol. 37, 1960, pp. 14-16.*

* cited by examiner

*Primary Examiner* — Deborah D Carr
(74) *Attorney, Agent, or Firm* — Sughrue Mion, PLLC

(57) ABSTRACT

A process is described for the purification of estolides for subsequent use as lubricants. This purification process comprises the removal of free fatty acids present in the estolide by liquid-liquid extraction using an alcohol, preferably ethanol or methanol, as solvent, where the total acid number of the estolide after purification is less than 1 mg KOH/g of sample, which endows it with characteristics of oxidation stability suitable for its use as a lubricant.

13 Claims, No Drawings

LIQUID-LIQUID EXTRACTION PROCESS FOR THE PURIFICATION OF ESTOLIDES FOR USE AS LUBRICANTS

CROSS REFERENCE TO RELATED APPLICATION

This application is a National Stage of International Application No. PCT/GB2009/001607 filed Jun. 26, 2009, claiming priority based on Brazilian Patent Application No. PI 0803361-7, filed Jun. 30, 2008, the contents of all of which are incorporated herein by reference in their entirety.

FIELD OF THE INVENTION

The invention relates to the field of continuous processes for the purification of estolides for use as lubricants. More specifically, the process comprises the removal of residual free fatty acids present in the estolide by liquid-liquid extraction, so as to lower its total acid number and consequently increase its oxidation stability.

BACKGROUND OF THE INVENTION

The main function of lubricating oils is to reduce the friction between parts that move relative to one another, by the formation of a fluid surface film, as well as to protect the parts against corrosion, and to assist in sealing and in the transfer of heat between the contacting surfaces. Usually these lubricants are prepared from a mixture of mineral or synthetic oils with various additives, the oils of mineral origin being those obtained by processes of distillation and refining of petroleum and the synthetic oils being those obtained by a process of synthesis using raw material different from the former.

The oils of mineral origin are not easily degraded or absorbed by the environment, which has in recent years aroused special interest in the advantages offered by substances derived from oils of vegetable origin, such as biodegradability and lower toxicity. However, these oils possess low thermal-oxidation and hydrolytic stability and in order to improve these properties, the fatty acids that make up the vegetable oils must undergo modifications in the carbon chain.

Estolides are derivatives of vegetable oils that have been shown to offer new promise for application as lubricants, due principally to their excellent properties at low temperatures, the pour point being one of the best indicators of such properties. The pour point is the lowest temperature at which the oil still flows freely under the action of gravity, after cooling in standardized conditions, and is extremely important when the lubricant must meet requirements of low-temperature viscosity.

Estolide is a generic name for linear oligomers of polyesters of fatty acids, in which the hydroxyl of a hydroxylated fatty acid is esterified by the carboxyl of another molecule of fatty acid.

U.S. Pat. No. 5,380,894 describes a process for the synthesis of estolides by the reaction between one or more unsaturated fatty acids in the presence of a catalyst, usually clay and water, in the temperature range from 230° C. to 250° C. and at initial pressure in the range from 200 kPa (30 psi) to 415 kPa (60 psi). The estolides thus produced can be used as lubricants, greases, plasticizers and printing inks, as well as in cosmetics.

U.S. Pat. No. 6,018,063 relates to a family of estolides derived from oleic acid, which are characterized by superior properties when used as lubricants. Among these properties, we may mention in particular: their high viscosity index, which avoids the use of additives that might cause problems connected with stability; their high oxidation stability compared with vegetable oils or fluids derived therefrom; and their low pour point, allowing them to be used as lubricants even at low temperatures.

In the cases described above, the estolide produced has double bonds in its structure. It is known, however, that its greater chain size permits better electronic distribution of the charges of the molecule, stabilizing the double bonds. Furthermore, the molecule of fatty acid added to the structure of the original ester tends to behave like a branching, generating a molecule with format similar to that of a ball of wool, making it difficult for oxygen to gain access to the double bonds of the structure, and consequently increasing the oxidation stability.

The synthesis of estolides from fatty acids gives a product with a large quantity of residual free fatty acids and consequently high total acid number (TAN).

In the specialized literature, the processes used for the removal of residual fatty acids involve vacuum distillation, in vertical distillation apparatus, at temperatures of approximately 200° C. and pressures of the order of 10 Pa (0.1 mbar). However, one of the problems encountered when using said purification process is the formation of epoxides or shorter-chain carboxylic acids, resulting from the oxidation of the double bonds present in the free fatty acids, which are highly unstable.

Isbell et al., in their article "Purification of meadowfoam monoestolide from polyestolide" (Industrial Crops and Products, Vol. 15, 145-154 (2002)), describe other processes for purification of estolides, including molecular distillation. The purpose of this is to separate the mono- and polyestolides, for subsequent use of the monoestolides in the formulation of cosmetics, as they possess suitable coloration for said use.

Therefore, at present no purification process for estolides is available in the prior art that involves simple and economical systems for the removal of residual fatty acids from estolides, such as the process described below.

SUMMARY OF THE INVENTION

The present invention relates to the purification of estolides by removal of residual free fatty acids by a continuous liquid-liquid extraction process, using a low molecular weight alcohol as solvent.

The continuous liquid-liquid extraction process promotes the intimate contact of a polar solvent and of a feed containing estolides and residual free fatty acids, at concentrations from 15% to 25% w/w, which imparts a TAN from 30 mg KOH/g to 50 mg KOH/g of sample. The polar solvent, preferably a short-chain alcohol, more preferably methanol or ethanol, removes the free fatty acids so that the final estolide has a value of TAN less than 1 mg KOH/g.

One of the advantages of using the liquid-liquid extraction process in the purification of estolides, compared with the processes available in the prior art, such as distillation, is the use of low temperatures, which avoids the formation of undesirable products resulting from the thermal decomposition or degradation of estolides and of fatty acids, which usually occurs at temperatures above 200° C.

DETAILED DESCRIPTION OF THE INVENTION

The continuous liquid-liquid extraction process described below has the purpose of removing residual free fatty acids that are present in a feed containing estolides.

Liquid-liquid extraction is a separation process that involves mass transfer between two immiscible liquids based on the distribution of a solute between the two phases and the partial miscibility of the liquids. The efficiency of extraction depends on the affinity of the solute for the solvent, the ratio between the phases and the number of extractions.

This methodology comprises simple stages, in which a variety of solvents can be used, providing a wide range of solubility and of selectivity.

In general, the choice of a solvent for a particular liquid-liquid extraction process must satisfy the following criteria:

a) Its density must be such as to permit separation by gravity between two immiscible phases of the process.

b) It must provide selective dissolution of the compound that we wish to extract.

c) it must be inert, so as not to react with the substances to be extracted.

d) It must, preferably, have a low boiling point, so as to permit its recovery and the isolation of the desired compound.

Among the aforementioned criteria, the most important one for the choice of the solvent is its affinity for the compound that we wish to extract, i.e. its selectivity, which in this case is related primarily to its polarity and hence to its solubility.

The fatty acids are large molecules, formed by a polar moiety (carboxyl) and a nonpolar moiety (carbon chain). This structure permits its solubility both in polar solvents and in nonpolar solvents. However, in the estolides formed by the linking together of fatty acids, the acid carboxyls are esterified, which gives the molecule less polarity and less affinity for polar solvents.

The solvents for use in the present invention are therefore polar solvents, more specifically low molecular weight alcohols, preferably C1-C4 alcohols, more preferably C1-C3 alcohols, as they extract the fatty acids selectively. Among the alcohols, the use of methanol and ethanol is preferred. Although methanol is more toxic than ethanol, the former possesses some advantages over the latter. Methanol, due to its greater polarity, displays greater affinity for the residual fatty acids, facilitating their removal.

Besides the choice of solvent, another variable to be observed in this process is the effect of temperature on the solubility of the fatty acids and of the estolide in the solvent.

The ideal temperature range for this process is from 20° C. to 30° C., since at temperatures below 20° C. the solubility of the fatty acids in methanol is less than 0.1 g of fatty acid per 100 g of methanol, which makes the process unviable. At temperatures above 30° C., the estolide dissolves in the alcohol, forming a single phase with the solvent, which prevents the use of the process.

Thus, the present invention relates to a continuous liquid-liquid extraction process whose purpose is to remove residual free fatty acids present in a feed of estolide, so as to lower the total acid number of the feed and consequently increase its oxidation stability, said process including the following stages:

a) supplying a feed for the process comprising estolides, and residual free fatty acids, wherein the residual free fatty acids are present in a concentration of from 15% to 25% by weight of feed;

b) adding a polar solvent to the feed, in a quantity sufficient to achieve a feed:alcohol ratio of from 3.5:1 to 4.5:1 (by weight) and stirring to keep the reaction mixture substantially homogeneous, in a temperature range of from 20° C. to 30° C.;

c) separating the phases: a first phase comprising the solvent and extracted fatty acids, and a second phase comprising the estolide and solvent;

d) sending the second phase to a vacuum still, operating at pressures in the range of from 350 mbar to 390 mbar and at temperatures in the range of from 30° C. to 60° C., for recovery of solvent for later reuse in the process;

e) recovering the solvent from the first phase by distillation, for later reuse in the process.

The process is preferably applied to feeds containing estolides and residual free fatty acids at concentrations in the range of from 15 to 25 wt. %, which gives them a TAN from 30 mg KOH/g to 50 mg KOH/g of feed.

The typical feeds for use in the process comprise estolides, synthesized from fatty acids of vegetable oils, such as soya, sunflower, canola and castor oil, constituted primarily of unsaturated fatty acids.

In the case of castor oil, for example, from 80% to 87% of its composition is ricinoleic acid,

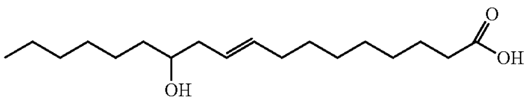

ricinoleic acid ricinoleic acid

The residual free fatty acids to be removed in the process described here are therefore unsaturated fatty acids, which are soluble in methanol at room temperature (temperatures close to 25° C.).

To avoid excessive consumption of the solvent, due to the low value of the partition constant, i.e. the small difference in solubility of the solute (fatty acids) in both liquids (estolide and alcohol), extraction is carried out in continuous mode.

In continuous mode, the solvent (alcohol) is permanently in contact with the feed, which is achieved by recirculation of the solvent. Recirculation makes it possible to utilize the same volume of solvent for a larger number of extractions, thus increasing the efficiency of separation.

The feed containing estolides after the purification process possesses a total acid number of less than 1 mg KOH/g of feed, and although the mineral lubricants currently being marketed have a specification that defines maximum TAN of 0.05 mg KOH/g of sample, the significant decrease in the values of TAN for these estolides, as shown in Table 1 of Example 2, demonstrates the efficiency of the extraction process described here.

The examples given below illustrate the purification of feeds containing estolides with impurities of fatty acids by the liquid-liquid extraction process, and present comparative data on their characteristics as lubricants relative to conventional lubricants, without limiting the scope of the invention.

EXAMPLE 1

Ninety grams (90 g) of sample of estolide with TAN=40 mg KOH/g of sample were added to a conventional extractor containing 1 L of methanol. 2 L of methanol was put in a distillation flask, and heated to 64° C., promoting distillation of the alcohol. After liquefaction in the condenser, the alcohol was mixed with the estolide in the extractor, dissolving a portion of the free fatty acids. After 5 hours, the estolide-methanol mixture was withdrawn from the extractor, and was submitted to distillation at reduced pressure to remove the alcohol. Distillation is carried out at a pressure of 37.3 kPa (373 mbar) and a temperature of 40° C. After distillation the acid number of the estolide is 0.7 mg KOH/g of sample.

EXAMPLE 2

Comparison of the properties of the purified estolides and of commercially available mineral lubricants.

Table 1 shows the physicochemical properties corresponding to the estolides (TAN=46 mg KOH/g of sample), purified estolides (TAN=1.2 mg KOH/g of sample) and commercially available mineral lubricants (NL GI, NL GII and naphthenics), demonstrating the increase in oxidation stability obtained by purification of the estolide by liquid-liquid extraction with methanol as solvent.

TABLE 1

| | TAN (mg KOH/g) | vis@40° C. ($10^{-6}$ $m^2/s$)[1] | VI[2] | PP[3] (° C.) | Stability[4] (min) |
|---|---|---|---|---|---|
| Estolide[5] | 46 | 26 | 192 | −40 | 22 |
| Estolide[6] | 1.2 | 46 | 241 | −52 | 241 |
| NL GI | <0.05 | 29 | 101 | −6 | 180 |
| NL GII | <0.05 | 30 | 110 | −21 | 369 |
| Naphthenic | <0.05 | 20 | 30 | −42 | 180 |

[1]Analyses of viscosity, performed at 40° C.;
[2]Viscosity index calculated for the fluids;
[3]Pour point;
[4]Test of oxidation stability, performed in rotary pump, with 2% of biodegradable additive;
[5]Estolide before purification;
[6]Estolide after purification.

These results demonstrate the advantages of the process of purification of estolides by liquid-liquid extraction, since it leads to a higher value of oxidation stability of the estolide to be used as lubricant, thus increasing the period of time required between the scheduled changes of a lubricant in a system.

The invention claimed is:

1. A liquid-liquid extraction process for the purification of estolides comprising:

a) supplying a feed for the process comprising estolides, and residual free fatty acids, wherein the residual free fatty acids are present in a concentration of from 15 to 25% by weight of feed;

b) adding a polar solvent to the feed, in a quantity sufficient to achieve a feed:polar solvent ratio of from 3.5:1 to 4.5:1 (by weight) and stirring to keep the reaction mixture substantially homogeneous, in a temperature range of from 20° C. to 30° C.;

c) separating the phases: a first phase comprising the solvent and extracted fatty acids, and a second phase, comprising the estolide and solvent;

d) sending the second phase to a vacuum still, operating at pressures in the range of from 350 mbar to 390 mbar and at temperatures in the range of from 30° C. to 60° C., for recovery of solvent for later reuse in the process; and e) recovering the solvent from the first phase by distillation, for later reuse in the process.

2. The process according to claim 1, wherein the feed for the process has a total acid number in the range of from 30 mg KOH/g to 50 mg KOH/g of feed.

3. The process according to claim 1, wherein the feed comprises estolides synthesized from vegetable oils.

4. The process according to claim 1, wherein extraction is carried out in continuous mode.

5. The process according to claim 1, wherein the total acid number of the feed after the process is less than 1 mg KOH/g of feed.

6. The process according to claim 1, wherein the polar solvent comprises one or more low molecular weight alcohols.

7. The process according to claim 6, wherein the one or more low molecular weight alcohols are methanol and/or ethanol.

8. The process according to claim 1, wherein the polar solvent is added to the feed in a quantity sufficient to achieve a feed:alcohol ratio of about 4:1.

9. A liquid-liquid extraction process for the purification of estolides for use as lubricants, comprising the following stages:

a) supplying a feed for the process consisting of estolides, containing residual free fatty acids at concentrations varying from 15 to 25 wt. %;

b) adding a polar solvent to the feed at a ratio of 4:1 (by weight) of feed:polar solvent, with stirring, keeping the reaction mixture homogeneous, in a temperature range from 20° C. to 30° C.;

c) separating the phases into an upper phase composed of the solvent and the fatty acids extracted, and a lower phase, composed of the estolide and solvent;

d) sending the lower phase to a vacuum still, operating at pressures varying in the range from 350 mbar to 390 mbar and temperatures in the range from 30° C. to 60° C. for recovery of the solvent; and e) recovering the solvent from the upper phase by distillation, for later reuse in the process.

10. The process according to claim 6, wherein the one or more low molecular weight alcohols are C1-C4 alcohols.

11. The process according to claim 6, wherein the one or more low molecular weight alcohols are C1-C3 alcohols.

12. The process according to claim 9, wherein the polar solvent is a low molecular weight alcohol.

13. The process according to claim 9, wherein the polar solvent is methanol or ethanol.

* * * * *